Jan. 20, 1970 H. C. BROWNELL Plant Pat. 2,959
ROSE PLANT
Filed March 21, 1968
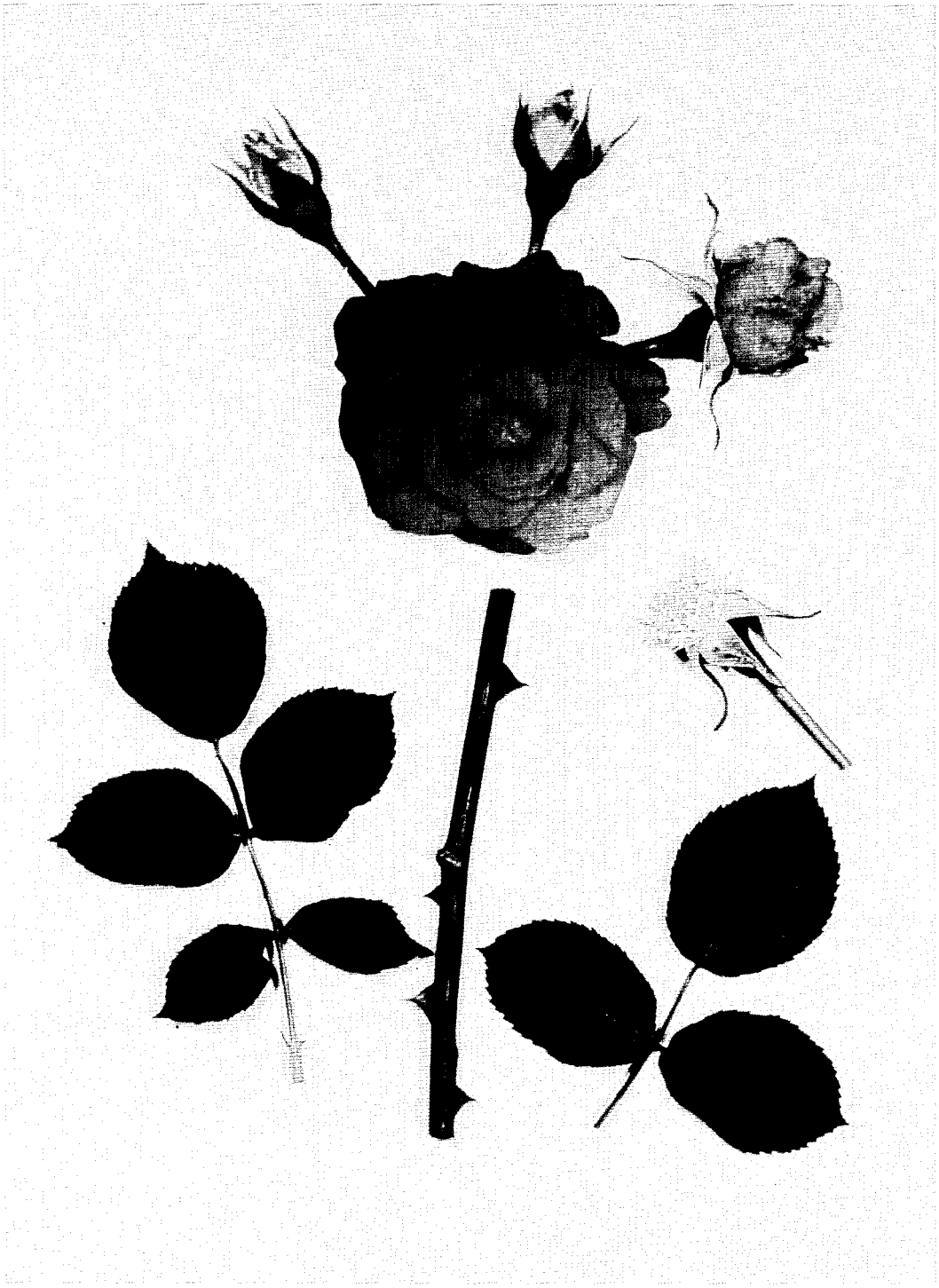
Herbert C Brownell

United States Patent Office

Plant Pat. 2,959
Patented Jan. 20, 1970

2,959
ROSE PLANT

Herbert C. Brownell, Little Compton, R.I. 02837

Filed Mar. 21, 1968, Ser. No. 715,111
Int. Cl. A01h *5/00*
U.S. Cl. Plt.—20 1 Claim My invention relates to roses and especially to a new, original and distinct variety of the class known commercially as "hybrid tea," and is a variant in that class, being a *Rosa wichuraiana* hybrid tea hybrid, produced by me and under my direction in the breeding grounds of my research gardens in Little Compton, R.I., by selection of variety variations and by cross pollination, which can be and has been asexually reproduced.

My new rose plant is new as to the following characteristics and especially as to their joint association with the characteristics inherited from *Rosa wichuraiana,* of hardiness, or immunity from serious injury on account of cold temperatures prevailing in certain parts of the northern United States:

The deep red color (ordinary dictionary definition) of its petals in combination with the unique brilliance thereof and their tendency to hold these colors under exposure, fading only very slightly under direct rays of the sun.

The novelty and variation within certain definite limits of the form of the bloom, the recurl of the petals as the flower opens, its character of holding its form for a long time and the petalage of the flowers;

Its unusual abundance of flowers, at bloom time and after early bloom time until frost;

Its character of ascending in height by recurrent branching and progressively longer stems from the base, if untrimmed, to reach to a height of eight feet or more in three years;

The character of producing many seven-leafleted leaves, which character seldom has obtained on hybrid teas not having *Rosa wichuraiana* ancestry;

And especially its characteristic of freedom from premature defoliation by blackspot, under certain definite conditions of exposure, without any cultural control.

The accompanying drawings shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Wilson's Horticultural Colour Chart, except where general color terms of ordinary dictionary significance are obvious:

Type: Hardy; bush; outdoor; seedling; for cut flowers and garden decoration.
Class: Hybrid tea.
Breeding: Seedling.
*Seed parent.*—Red Duchess—Plant Patent Number 846.
*Pollen parent.*—Queen Elizabeth—Plant Patent Number 1,259.
Propagation: Holds its distinguishing characteristics through succeeding propagations by budding.

FLOWER

Locality where grown and observed: Little Compton, R.I., U.S.A.
Flowers borne: Singly and in clusters on stems of medium length and normal strength.
Quantity of bloom: Abundant, outdoors.
Continuity: Continuous during growing season until frost.
Fragrance: Slight to moderate.
Bud:

*Peduncle.*—Average length; medium caliper; moderate number of very fine red haris. Color—Pod Green, Plate 061/1.
*Before calyx breaks.* — Size — medium. Form — pointed; with slender foliaceous parts extending beyond tip of the bud equal to ⅓ or more of its length. Color—Lettuce Green 861/3 overlaid with Garnet Brown 00918.
*As calyx breaks.*—Color: outside of petal—Currant Red 821; inside of petal—Currant Red 821/3.
*As first petal opens.*—Size—medium. Form—globular. Color: outside—Cardinal Red 822/3; inside—Cardinal Red 822/1.
Bloom:
*Size (when fully open).*—Large; from 4 to 4¾ inches.
*Petalage.*—Double from 40 to 45 petals; arranged regularly.
*Form.*—Globular, becoming cupped. Petals recurl as bloom opens.
Petals:
*Texture.*—Thick; leathery.
*Shape.*—Orbiculate; no notches.

This description of a newly opened flower was made from a rose grown outdoors at Little Compton, R.I. in the month of August.

*Color.*—Outer pertal: outside surface—Cardinal Red 822; inside surface—Cardinal Red 822/3. Inner petal; outside surface—Crimson 22/1. inside surface—Rose Red 724. At base of petals a small section Canary Yellow 2/2.
*Flower longevity.*—On bush in garden 5 or 6 days in August. Cut roses grown outdoors and kept at living room temperature 3 or 4 days in August.

REPRODUCTIVE ORGANS

Stamens: Average number; arranged slightly irregular.
Filaments: Medium number; most with anthers; medium length. Color—Maize Yellow 607.
Anthers: All open at once; medium sized. Color—Maize Yellow 607.
Pollen: Abundant.
Pistils: Many.
Styles: Uneven; medium length; average caliper.
Ovaries: Usually all enclosed in calyx.
Hips: Short; globular; smooth. Color (mature)—Lettuce Green 861/2.
Sepals: Permanent; long pointed. Color: outside—Lettuce Green 861/1; inside—Pod Green 061/3.

PLANT

Foliage:
*Leaves.*—Compound of usually 3 to 7 leaflets; normal quantity; medium size.
*Leaflets.*—Shape—ovate and occasionally mucronate.
*Color.*—Mature: upper surface—Parsley Green 00962; under surface—Sage Green 00861/1.
*Rachis (the supporting stem of the compound leaf).*—Average size. Upper side—grooved. Under side—smooth with one or two small prickles.
*Stipules.*—Medium; average width; points of short length, the upper of which normally form an angle of 90 degrees.
*Disease resistance.*—Better-than-average resistance to black-spot and mildew as compared with other varieties grown under comparable conditions at Little Compton, R.I.
Growth:
*Habit.*—Bushy; upright-spreading; much-branched.
*Growth.*—From very free to vigorous.
*Canes.*—Medium caliper.

*Stems.—Color*—Lettuce Green 861. Few prickles; short; hooked slightly downward.

I claim:

1. A new and distinct variety of rose plant of the hybrid tea type, substantially as herein shown and described, characterized particularly as to novelty by its vigorous habit of growth, abundant foliage, its resistance to mildew and blackspot, and its ability to withstand moderate sub-zero temperatures in combination with its hybrid tea character and its *Rosa wichuraiana* ancestry.

No reference cited.

ROBERT E. BAGWILL, Primary Examiner